United States Patent
Nishide et al.

(10) Patent No.: US 6,862,336 B2
(45) Date of Patent: Mar. 1, 2005

(54) X-RAY CT APPARATUS AND METHOD OF CONTROLLING IT

(75) Inventors: Akihiko Nishide, Tokyo (JP); Masaya Kumazaki, Tokyo (JP); Masatake Nukui, Tokyo (JP)

(73) Assignee: GE Medical Systems Global Technology, LLC, Waukesha, WI (US)

( * ) Notice: Subject to any disclaimer, the term of this patent is extended or adjusted under 35 U.S.C. 154(b) by 187 days.

(21) Appl. No.: 10/382,007

(22) Filed: Mar. 5, 2003

(65) Prior Publication Data

US 2003/0169842 A1 Sep. 11, 2003

(30) Foreign Application Priority Data

Mar. 6, 2002 (JP) ........................................ 2000-060631

(51) Int. Cl.[7] ................................................. A61B 6/03
(52) U.S. Cl. .............................. 378/8; 378/15; 378/19; 378/901
(58) Field of Search ............................. 378/4, 8, 15, 19, 378/901

(56) References Cited

U.S. PATENT DOCUMENTS

| | | | |
|---|---|---|---|
| 4,626,991 A | 12/1986 | Crawford et al. | |
| 4,680,709 A | 7/1987 | Srinivasan et al. | |
| 6,466,639 B2 | 10/2002 | Nukui et al. | |
| 2003/0169842 A1 * | 9/2003 | Nishide et al. | 378/4 |

* cited by examiner

*Primary Examiner*—David V Bruce
(74) *Attorney, Agent, or Firm*—Carl B. Horton, Esq.; Armstrong Teasdale LLP

(57) ABSTRACT

For the purpose of determining an offset of the position of an X-ray tube from a prespecified position, and correcting axially projected data D1 and pixel projection data D2 based on the determined offset, proper axially projected data D1 can be obtained by an X-ray focal spot 2102 and a detector 2103 by determining axially projected data D1 at a point 2104 using projection data D0 obtained by a channel that detects an X-ray emitted from the X-ray focal spot 2102 and passing through the point 2104, and shifting the determined axially projected data D1 by a distance DIS1 in the (+)-direction of the x-axis.

18 Claims, 25 Drawing Sheets

| | view=45° -Δview | | |
| | view= | | |
| | view=0° | | |
| | view= | | |
| view= -45° | | | |
| pt | ch(pt) | k1(pt) | k2(pt) |
| 0 | | | |
| 1 | | | |
| 2 | | | |
| Pe | | | |

| view=45° -Δview | | | | | |
| view= | | | | | |
| view=0° | | | | | |
| view= | | | | | |
| view= -45° | | | | | |
| y | R (y) | Δ pt | str_pt | str_x | end_x |
| 0 | | | | | |
| 1 | | | | | |
| 2 | | | | | |
| | | | | | |
| Ye | | | | | |

$-45° \leq \text{view} < 45°$ $\quad 135° \leq \text{view} < 225°$
D1 (view, pt) = k1(pt) x D0 (view, ch(pt)+1) + k2(pt) x D0 (view, ch(pt))

-45° ≦ view<45°   135° ≦ view<225°

$-45° \leq \text{view} < 135°$  $225° \leq \text{view} < 315°$

D1 (view, pt) = k1(pt) × D0 (view, ch(pt)+1) + k2(pt) × D0 (view, ch(pt))

$-45° \leq view < 45°$   $135° \leq view < 225°$ $R(x) = (r1(x)/r2(x))^2$ $D2(view, x, y) = R(x) \times D1(view, str\_pt + (y-str\_y)\Delta pt)$ $D2(x, y) - \underset{view}{\Sigma} D2(view, x, y)$

70

-45° ≤ view<45°    135° ≤ view<225°

45° ≦ view<135° or
225° ≦ view<315°

| pt | ch (pt) | k1 (pt) | k2 (pt) | k3 (pt) |
|---|---|---|---|---|
| 0 | | | | |
| 1 | | | | |
| 2 | | | | |
| Pe | | | | |

(Stacked views: view= -45°, view=, view=0°, view=, view=45°)

D1 (view, pt) = k1(pt) x D0 (view, ch(pt)+2) + k2(pt) x D0 (view, ch(pt)+1) + k3(pt) x D0 (view, ch(pt))

FIG. 25
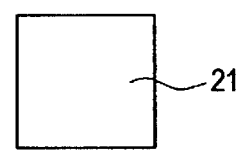
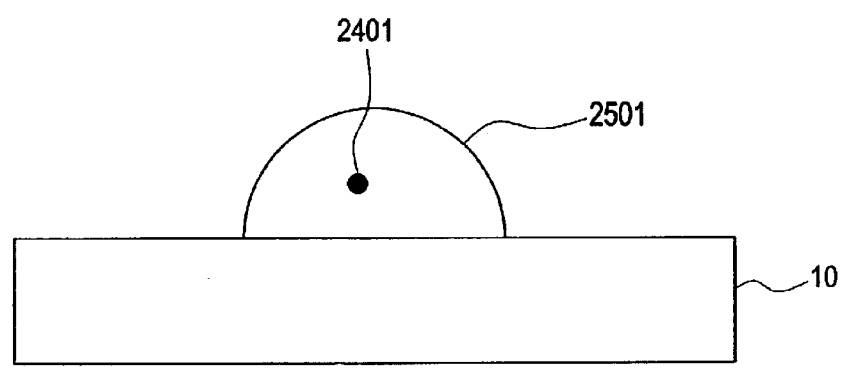
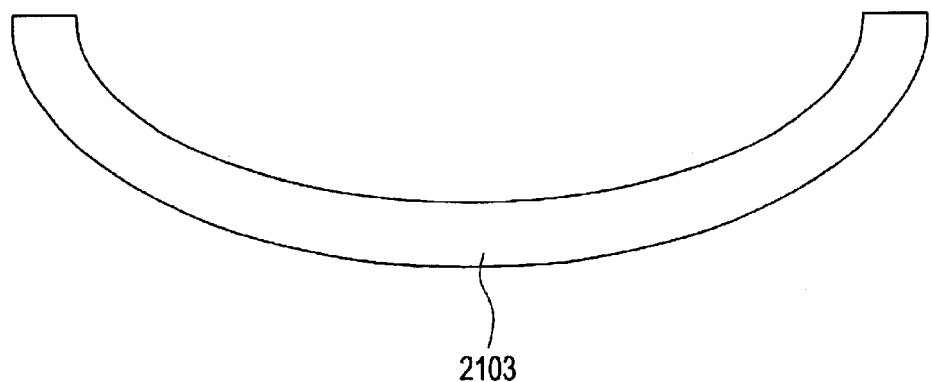

X-RAY CT APPARATUS AND METHOD OF CONTROLLING IT

CROSS REFERENCE TO RELATED APPLICATIONS

This application claims the benefit of Japanese Application No. 2002-060631 filed Mar. 6, 2002.

BACKGROUND OF THE INVENTION

The present invention relates to an X-ray CT apparatus and a method of controlling it.

The current mainstream X-ray CT apparatus implements a filtered backprojection technique involving processes of data collection, preprocessing, filtering, backprojection processing, and post-processing to thereby reconstruct an image.

Conventional backprojection processing is disclosed in, for example, Japanese Patent Application Laid Open No. H8-187241 and U.S. Pat. No. 5,414,622.

In such backprojection processing, projection data D0(view, ch) obtained by a fan beam represented by a view angle view and a detector channel ch is subjected to a calculation for projecting the projection data D0(view, ch) onto coordinates (x, y) of a pixel constituting a reconstruction region to determine pixel projection data D2(x, y), and the pixel projection data D2(x, y) for all views used in image reconstruction are added to determine backprojection data D3(x, y).

The conventional method of determining backprojection data D3, however, often employs an arctan lookup table LUT to speed up a calculation of determining a distance from an X-ray focal spot to a reconstruction plane. At that time, it is assumed that the positional relationship between the X-ray focal spot and X-ray detector is in proper alignment; specifically, that the X-ray focal spot lies on a centerline (or if ¼ channel shifting is applied, a centerline shifted by a ¼ channel) of the arc-shaped X-ray detector. FIG. 20 shows the X-ray focal spot and the X-ray detector with their positional relationship in proper alignment.

In FIG. 20, reference numeral 2000 designates an X-ray focal spot; 2001 designates an X-ray detector; 2001a and 2001b designate reference channels of the X-ray detector 2001; and 2002a and 2002b designate X-rays impinging upon the reference channels 2001a and 2001b.

The reference channels 2001a and 2001b are channels at ends among those of the X-ray detector 2001, and they detect X-rays emitted from the X-ray focal spot 2000 not passing through a subject. If the reference channels 2001a and 2001b detect the same amount of X-rays, the position of the X-ray focal spot 2000 and the position of the X-ray detector 2001 are considered to be in proper alignment. At the same time, the length of the X-ray 2002a (the straight-line distance from the X-ray focal spot 2000 to the reference channel 2001a) is equal to the length of the X-ray 2002b (the straight-line distance from the X-ray focal spot 2000 to the reference channel 2001b). However, such alignment is cumbersome and difficult to achieve precisely.

SUMMARY OF THE INVENTION

Therefore, an object of the present invention is to provide an X-ray CT apparatus and a method of controlling it involving determining the positional offset of an X-ray tube from a prespecified position, and correcting axially projected data D1 or pixel projection data D2 based on the determined offset.

To attain the object of the present invention, an X-ray CT apparatus of the present invention has, for example, a configuration below.

Specifically, the X-ray CT apparatus is comprised of: a gantry having an X-ray tube for emitting X-rays and a detector for detecting the X-rays emitted by said X-ray tube, said gantry outputting projection data D0 corresponding to an amount of the X-rays detected by said detector, represented by a view angle and a channel of said detector; and an operating console having axially projected data/pixel projection data calculating means for determining axially projected data D1 by projecting said projection data D0 obtained by said gantry onto a reference axis in a reconstruction region, and further determining pixel projection data D2 by projecting said axially projected data D1 onto coordinates of pixels constituting said reconstruction region, said operating console determining backprojection data D3 by adding said pixel projection data D2 determined by said axially projected data/pixel projection data calculating means for all views used in image reconstruction, and said CT apparatus is characterized in comprising: amount-of-offset measuring means for obtaining information indicative of an amount of offset of the position of said X-ray tube from a prespecified position; and correcting means for correcting the axially projected data D1 or pixel projection data D2 determined by said axially projected data/pixel projection data calculating means using the information indicative of the amount of offset obtained by said amount-of-offset measuring means.

Moreover, to attain the object of the present invention, a method of controlling an X-ray CT apparatus of the present invention has, for example, the following configuration.

Specifically, a method of controlling an X-ray CT apparatus that is comprised of: a gantry having an X-ray tube for emitting X-rays and a detector for detecting the X-rays emitted by said X-ray tube, said gantry outputting projection data D0 corresponding to an amount of the X-rays detected by said detector, represented by a view angle and a channel of said detector; and an operating console having axially projected data/pixel projection data calculating means for determining axially projected data D1 by projecting said projection data D0 obtained by said gantry onto a reference axis in a reconstruction region, and further determining pixel projection data D2 by projecting said axially projected data D1 onto coordinates of pixels constituting said reconstruction region, said operating console determining backprojection data D3 by adding said pixel projection data D2 determined by said axially projected data/pixel projection data calculating means for all views used in image reconstruction, is characterized in comprising: an amount-of-offset measuring step of obtaining information indicative of an amount of offset of the position of said X-ray tube from a prespecified position; and a correcting step of correcting the axially projected data D1 or pixel projection data D2 determined at said axially projected data/pixel projection data calculating step using the information indicative of the amount of offset obtained at said amount-of-offset measuring step.

According to the present invention, even if the position of an X-ray tube is offset from a prespecified position, axially projected data D1 and pixel projection data D2 obtained by the X-ray tube and a detector can be corrected using the offset.

Further objects and advantages of the present invention will be apparent from the following description of the preferred embodiments of the invention as illustrated in the accompanying drawings.

BRIEF DESCRIPTION OF THE DRAWINGS

FIG. 2 is a conceptional diagram of a lookup table 31 stored in a storage device 7.

FIG. 3 is a conceptional diagram of a lookup table 32 stored in the storage device 7.

FIG. 19 is a conceptional diagram of a lookup table 31'.

FIG. 25 is a diagram for explaining a method of setting a center pin.

DETAILED DESCRIPTION OF THE INVENTION

The present invention in accordance with preferred embodiments will now be described in detail with reference to the accompanying drawings.

[First Embodiment]

Figure 1:
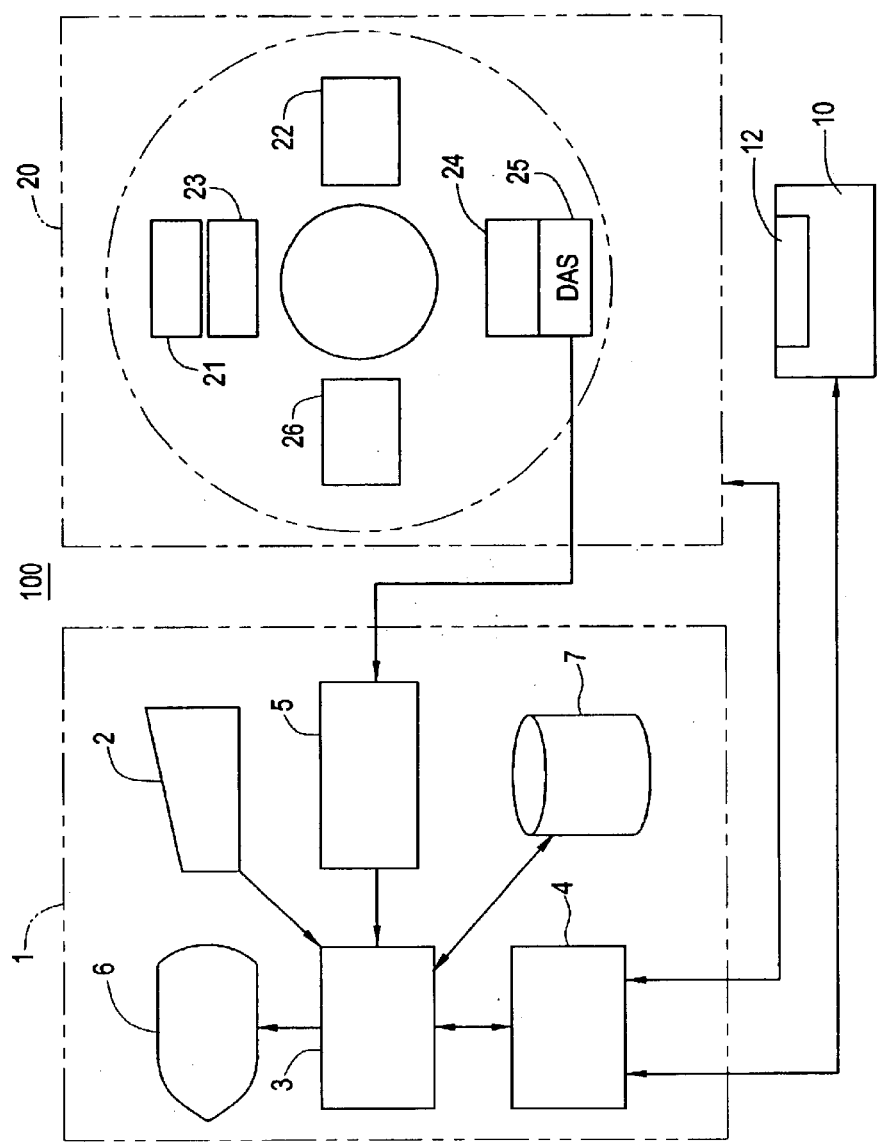
FIG. 1 is a block diagram showing the basic configuration of an X-ray CT apparatus in accordance with a first embodiment of the present invention.

FIG. 1 is a block diagram showing the basic configuration of an X-ray CT apparatus in accordance with a first embodiment of the present invention. The X-ray CT apparatus 100 comprises an operating console 1, an imaging table 10, and a gantry 20.

The operating console 1 comprises an input device 2 for accepting inputs by a human operator, a central processing apparatus 3 for executing backprojection processing which will be described later and the like, a control interface 4 for communicating control signals etc. with the imaging table 10 and gantry 20, a data collection buffer 5 for collecting projection data D0 acquired at the gantry 20, a CRT 6 for displaying an X-ray CT image (X-ray tomographic image) reconstructed from the projection data D0, and a storage device 7 for storing programs, data, and X-ray CT images.

The table apparatus 10 comprises a cradle 12 for laying thereon a subject and transporting the subject into/out of a bore (internal cavity portion) of the gantry 20. The cradle 12 is driven by a motor incorporated in the table apparatus 10.

The gantry 20 comprises an X-ray tube 21, an X-ray controller 22, a collimator 23, a detector 24, a DAS (data acquisition system) 25, and a rotation controller 26 for rotating the X-ray tube 21 around the body axis of the subject.

FIG. 2 is a conceptual diagram of a lookup table 31 stored in the storage device 7.

In the lookup table 31, a coordinate pt of axially projected data D1 on a projection axis (reference axis) for each view angle view in a view angle range of −45°≦view<45°, an address of projection data D0, i.e., a channel index ch(pt), for determining the axially projected data D1(view, pt), and interpolation factors k1(pt) and k2(pt) are stored beforehand.

The symbol Δview is a step angle for the view angle (i.e., the view angle difference between adjacent views). The symbol Pe is the maximum of pt, which will be described later with reference to FIG. 6.

FIG. 3 is a conceptual diagram of a lookup table 32 stored in the storage device 7.

Figure 11:
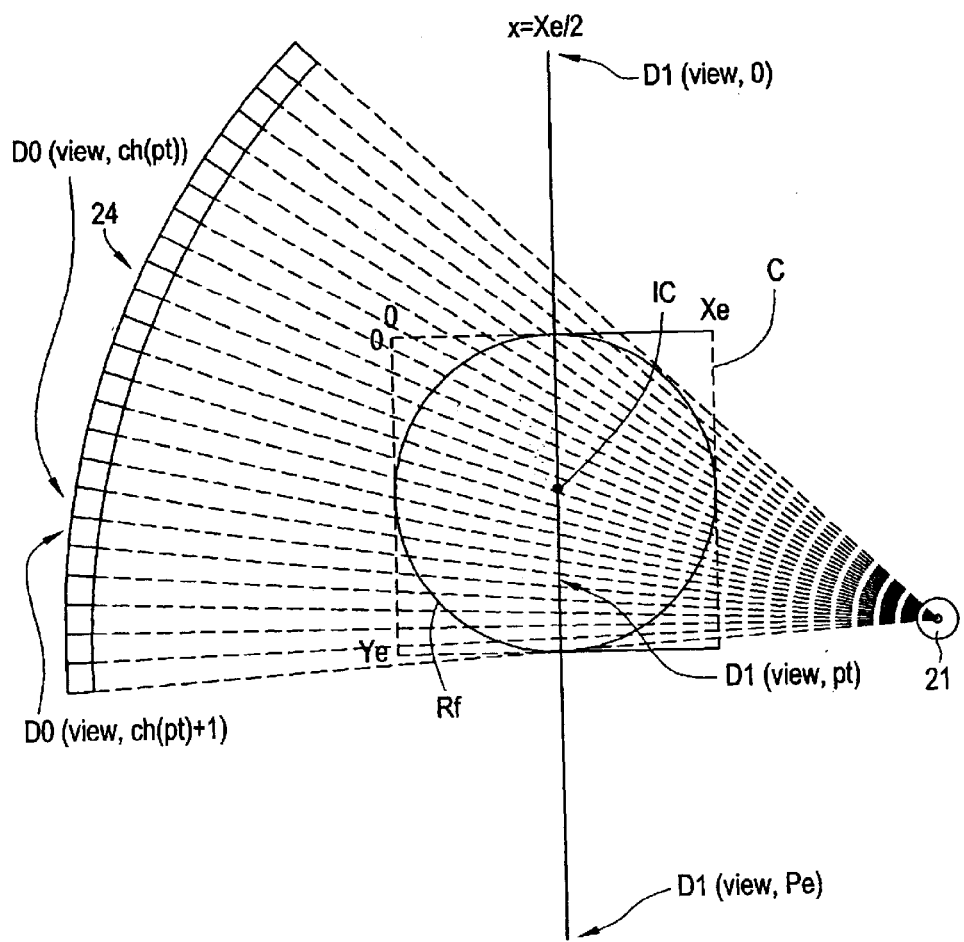
FIG. 11 is a diagram for explaining processing at Step S56.

In the lookup table 32, a y-coordinate of pixel projection data D2 for each view angle view in a view angle range of −45°≦view<45°, a distance factor R(y) as a parameter for determining one pixel projection datum D2(y, x) from one axially projected datum D1, a sampling pitch Δpt, the number of sampling points str__pt, a start address str__x, and an end address end__x are calculated and stored in the lookup table LUT beforehand. These parameters will be described later with reference to FIG. 11. The symbol Ye is the maximum of the y-coordinate in a reconstruction region Rf, as shown in FIG. 11.

Figure 4:
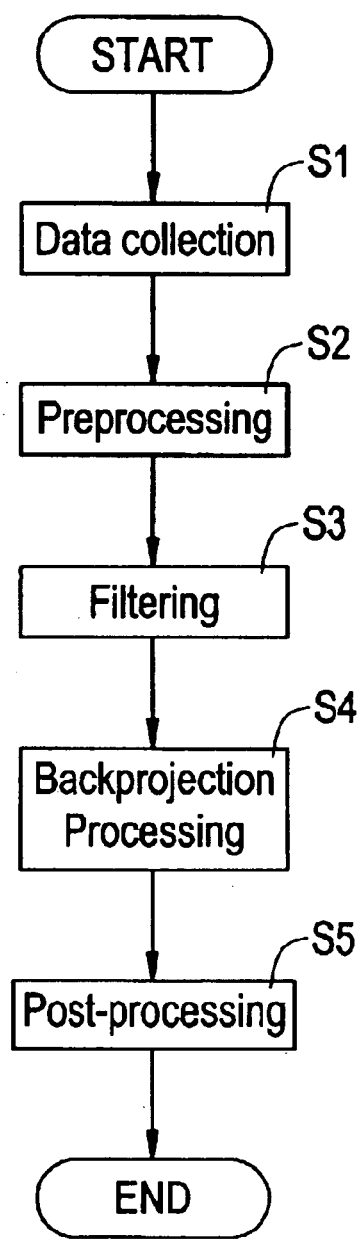
FIG. 4 is a flow chart showing the overall flow of the operation of an X-ray tube 100.

FIG. 4 is a flow chart showing the overall flow of the operation of the X-ray tube 100. In Step S1, projection data D1(view, ch) represented by the view angle view and the detector channel ch are collected while rotating the X-ray tube 21 and detector 24 around the subject to be imaged.

In Step S2, preprocessing (e.g., offset correction, DAS gain correction, and sensitivity correction) is performed on the projection data D0(view, ch).

In Step S3, filtering is performed on the preprocessed projection data D0(view, ch). Specifically, the data is Fourier-transformed, is filtered (subjected to a reconstruction function), and is inversely Fourier-transformed.

In Step S4, backprojection processing which will be described later is performed on the filtered projection data D0(view, ch) to determine backprojection data D3(x, y). The backprojection processing will be described later with reference to FIG. 5.

In Step S5, post-processing (Ring Fix, IBO, ANR) is performed on the backprojection data D3(x, y) to produce a CT image.

Figure 5:
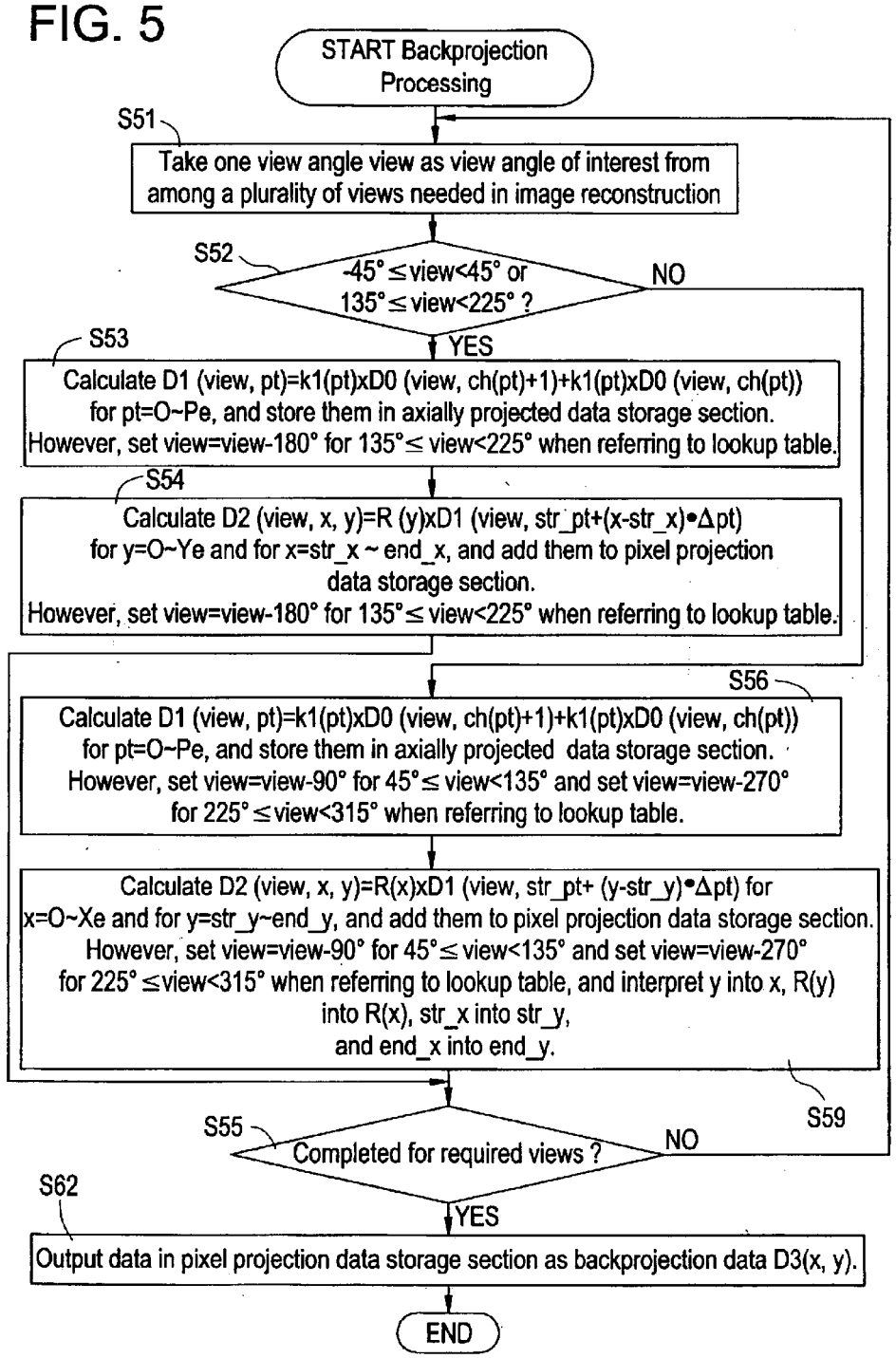
FIG. 5 is a flow chart showing the detailed flow of backprojection processing (Step S4).

FIG. 5 is a flow chart showing the detailed flow of the backprojection processing (Step S4).

In Step S51, one view angle view is taken as a view angle of interest from among a plurality of views needed in image reconstruction.

In Step S52, if the view angle of interest view is $-45° \leq \text{view} < 45°$ or $135° \leq \text{view} < 225°$, the process goes to S53; otherwise (i.e., if it is $45° \leq \text{view} < 135°$ or $225° \leq \text{view} < 315°$), goes to Step S56.

In Step S53, a lookup table 31 corresponding to the view angle view is referred to, to first obtain a channel index ch(0) corresponding to Pt=0 from the channel indices ch(pt), and then retrieve the filtered projection data D0(view, ch(0)+1) and D0(view, ch(0)). In addition, interpolation factors k1(0) and k2(0) are read out from k1(pt) and k2(pt). Then, axially projected data D1(view, 0) is calculated according to the following equation, and is stored in the storage device 7:

$$D1(\text{view},0)=k1(0) \times D0(\text{view},ch(0)+1)+k2(0) \times D0(\text{view},ch(0)).$$

If ch(pt) is not defined for a certain pt, this pt is skipped and the next pt is taken.

Moreover, for $135° \leq \text{view} < 225°$, a lookup table 31 corresponding to a view angle view=view−180 is referred to.

Figure 6:
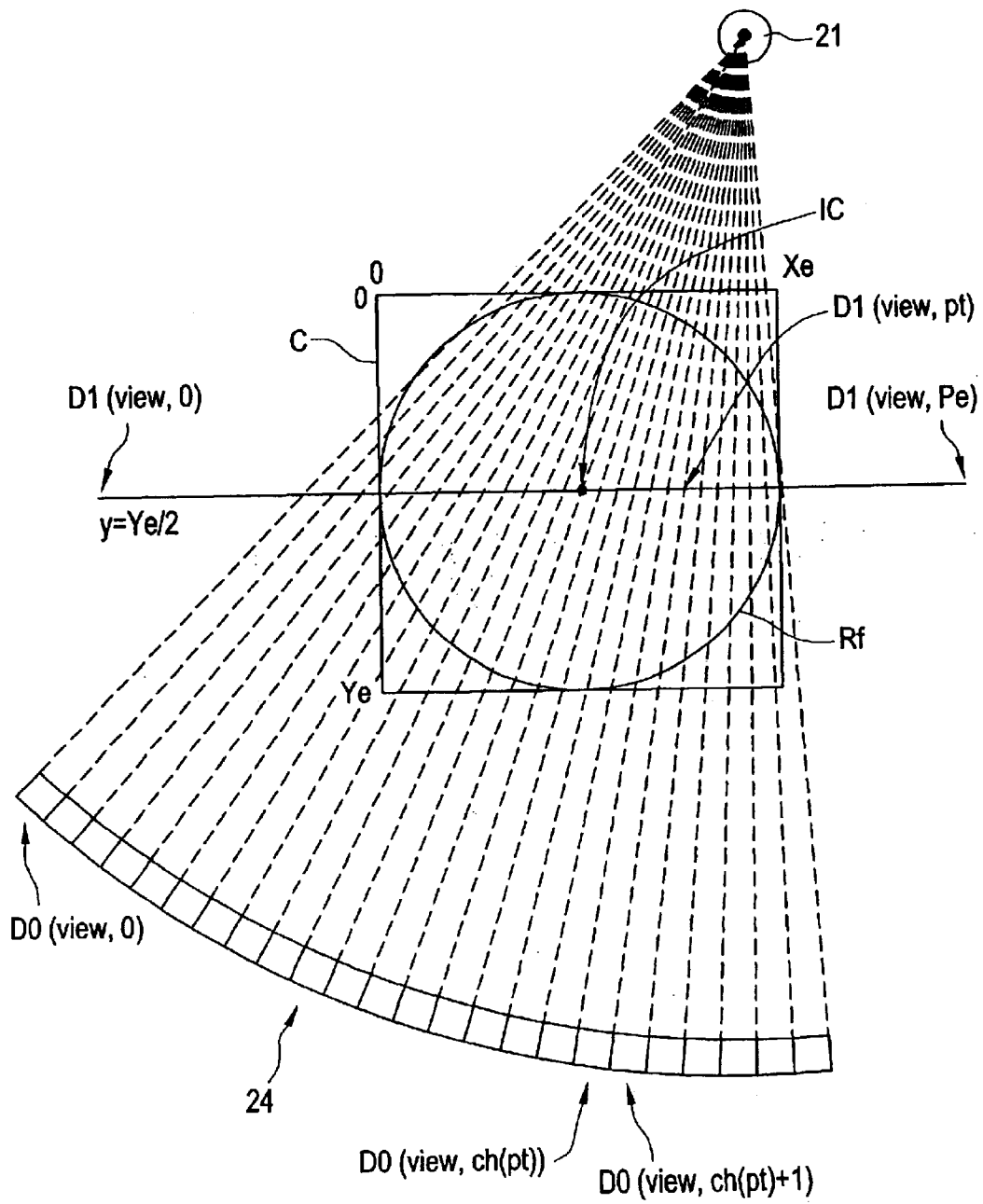
FIG. 6 is a diagram for explaining processing at Step S53.

FIG. 6 is a diagram for explaining the processing at Step S53. Step S53 corresponds to a calculation for determining axially projected data D1(view, pt) lining up along a projection axis represented by a straight line y=Ye/2 parallel to the x-axis direction and passing through an isocenter IC, from projection data D0(view, ch) lining up at arc-shaped geometrical positions corresponding to the arc-like shape of the detector 24.

Figure 7:
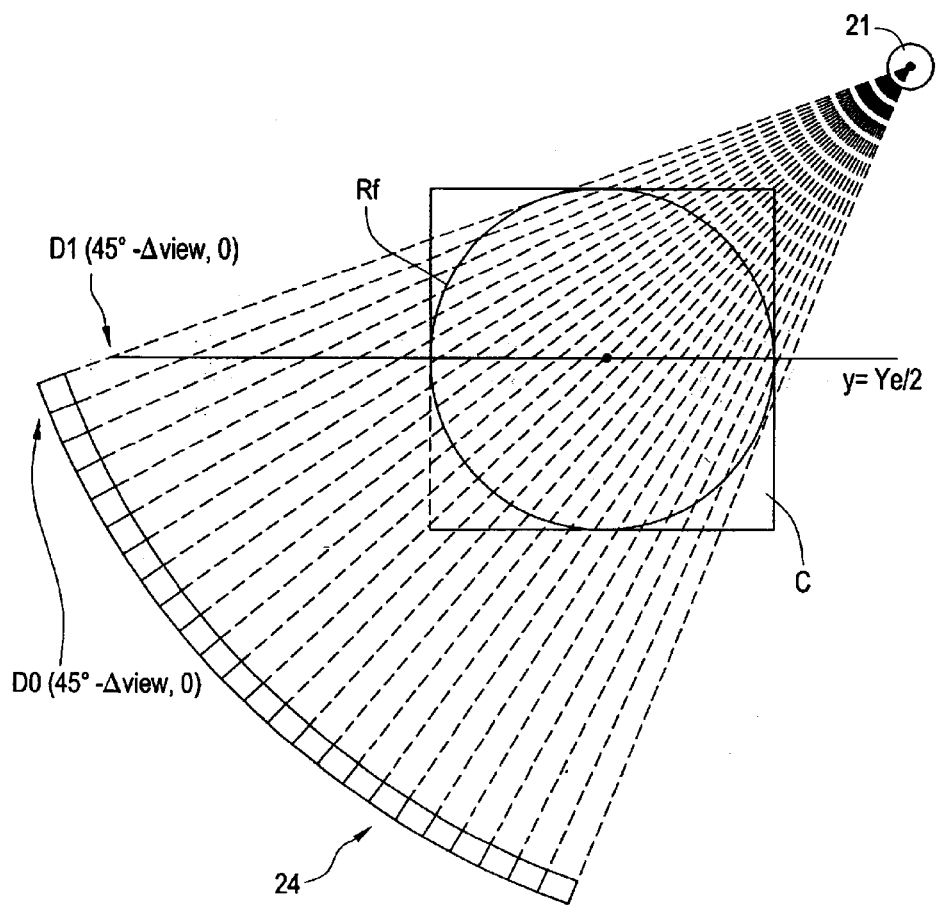
FIG. 7 is a diagram for explaining a position of axially projected data D1(view, 0).

The position of the axially projected data D1(view, 0) is defined at a view angle view=45−Δview, as shown in FIG. 7. Note that view=0° when the direction of the fan beam is parallel to the y-axis direction, and the view angle step is represented by Δview.

Figure 8:
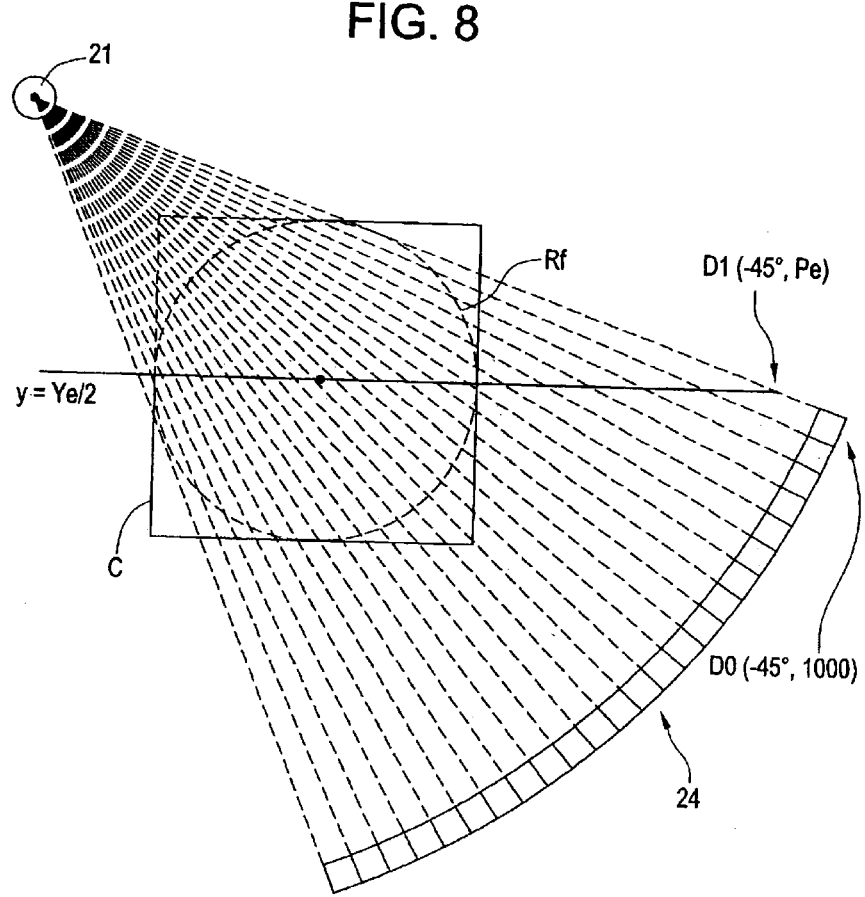
FIG. 8 is a diagram for explaining a position of axially projected data D1(view, Pe).

The position of the axially projected data D1(view, Pe) is defined at a view angle view=−45°, as shown in FIG. 8. Note that the detector 24 has 1,000 channels here.

As can be seen from FIGS. 6–8, one view has a projection axis portion contained in the fan beam and a projection axis portion not contained in the fan beam. No value of ch(pt) is set in the lookup table 31 for pt corresponding to a projection axis portion not contained in the fan beam.

Returning to FIG. 5, in Step S54, a lookup table 32 corresponding to a view angle view is referred to, to first obtain Δpt, str_pt and str_x for y=0, set x=str_x, and then retrieve axially projected data D1(view, str_pt) from the storage device 7. In addition, a transformation factor R(y) is read out. Then, pixel projection data D2(view, str_x, 0) is calculated according to the following equation:

$$D2(\text{view},str\_x,0)=R(0) \times D1(\text{view},str\_pt).$$

The data is added to D2(x, y) stored in the storage device 7:

$$D2(str\_x,0)=\Sigma D2(\text{view},str\_x,0),$$

wherein Σ represents a summation over view. Similarly, pixel projection data D2(view, x, 0) are calculated for x=str_x+1−end_x, and added to the pixel projection data D2(x, 0) stored in the storage device 7 according to the following equations:

$$D2(\text{view},x,0)=R(0) \times D1(\text{view},str\_pt+(x-str\_x)\Delta pt), \text{ and}$$

$$D2(x,0)=\Sigma D2(\text{view},x,0),$$

wherein Σ represents a summation over view. Next, pixel projection data D2(view, x, y) are similarly calculated for y=1−Ye, and added to the pixel projection data D2(x, y) stored in the storage device 7 according to the following equations:

$$D2(\text{view},x,y)=R(0) \times D1(\text{view},str\_pt+(x-str\_x) \times \Delta pt), \text{ and}$$

$$D2(x,y)=\Sigma D2(\text{view},x,y),$$

wherein Σ represents a summation over view. For $135° \leq \text{view} < 225°$, a lookup table 32 corresponding to a view angle view=view−180° is referred to.

Figure 9:
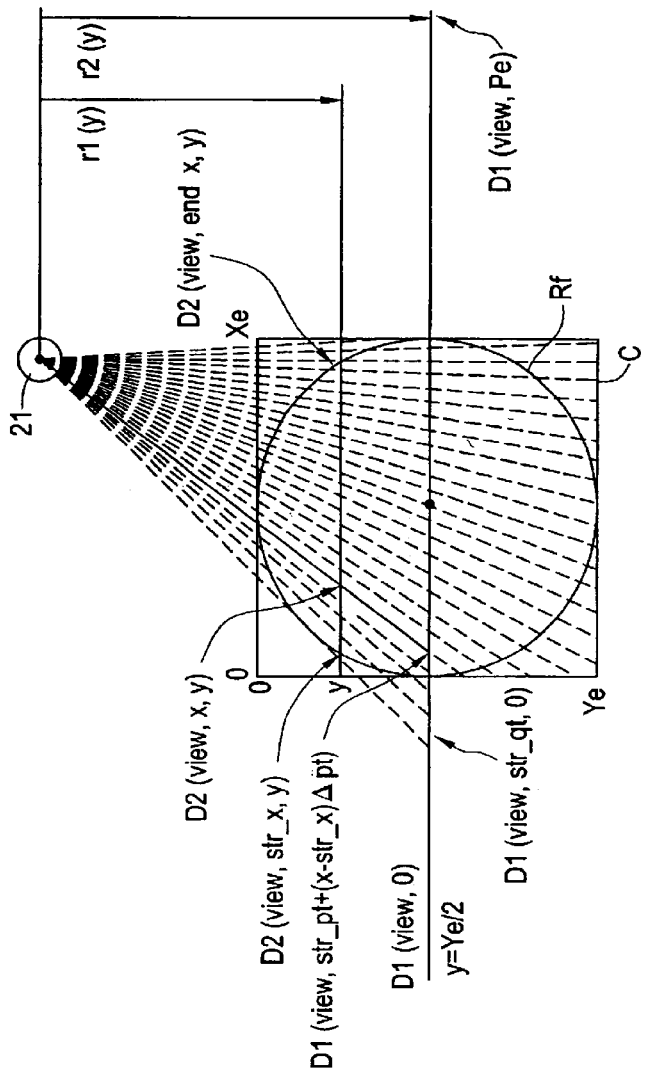
FIG. 9 is a diagram for explaining processing at Step S54.

FIG. 9 is a diagram for explaining the processing at Step S54. Pixel projection data D2 is calculated along a straight line parallel to the x-axis from the axially projected data D1 on the projection axis y=Ye/2, and this process is repeated for Y=0−Ye.

Figure 10:
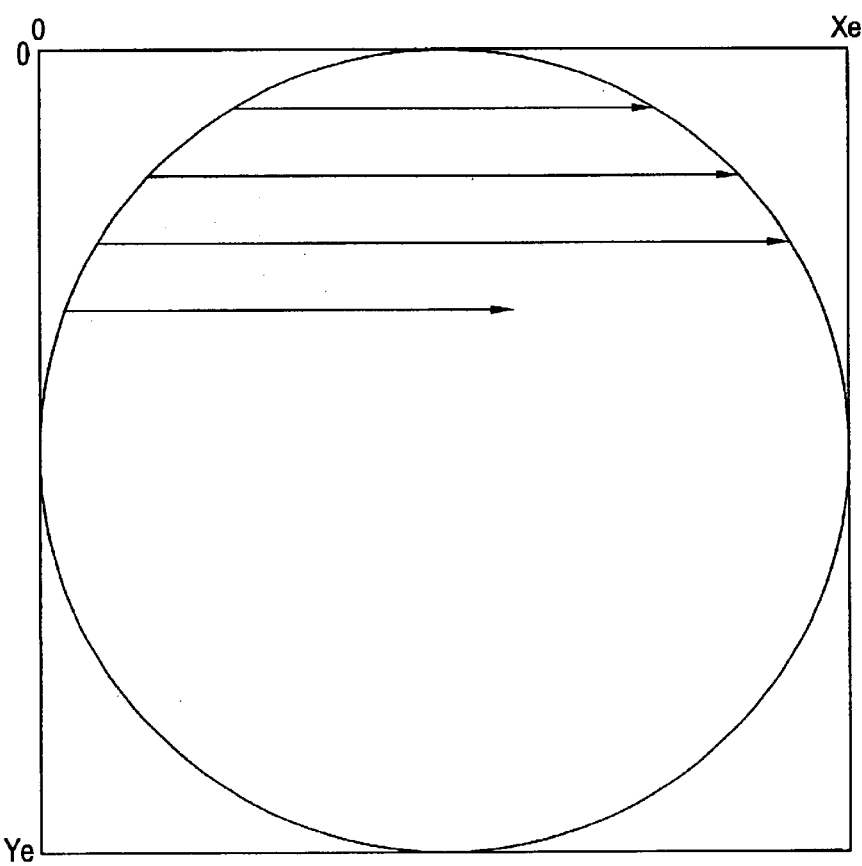
FIG. 10 is a conceptional diagram of a pixel projection data storage section 70 in the storage device 7.

FIG. 10 is a conceptual diagram of a pixel projection data storage section 70 in the storage device 7. The pixel projection data D2 is added along a straight line parallel to the x-axis, and this process is repeated for Y=0−Ye.

Returning to FIG. 5, in Step S55, if Steps S51–S59 have not been repeated for all views needed in image reconstruction, the process goes back to Step S51; and if Steps S51–S59 have been repeated for all views needed in image reconstruction, the process goes to Step S62.

In Step S56, if the view angle falls within $45° \leq \text{view} < 135°$, a lookup table 31 corresponding to a view angle view=view−90° is referred to, and if the view angle falls within $225° \leq \text{view} < 315°$, a lookup table 31 corresponding to a view angle view=view−270° is referred to. Then, axially projected data D1(view, pt) are calculated for pt=0−Pe similarly to Step S53 according to the following equation:

$$D1(\text{view},pt)=k1(pt) \times D0(\text{view},ch(pt)+1)+k2(pt) \times D0(\text{view},ch(pt)).$$

If ch(pt) is not defined for a certain pt, this pt is skipped and the next pt is taken.

FIG. 11 is a diagram for explaining the processing at Step S56. Step S56 corresponds to a calculation for determining axially projected data D1(view, pt) lining up along a projection axis represented by a straight line x=Xe/2 parallel to the y-axis direction and passing through the isocenter IC, from projection data D0(view, ch) lining up at arc-shaped geometrical positions corresponding to the arc-like shape of the detector 24.

Figure 12:
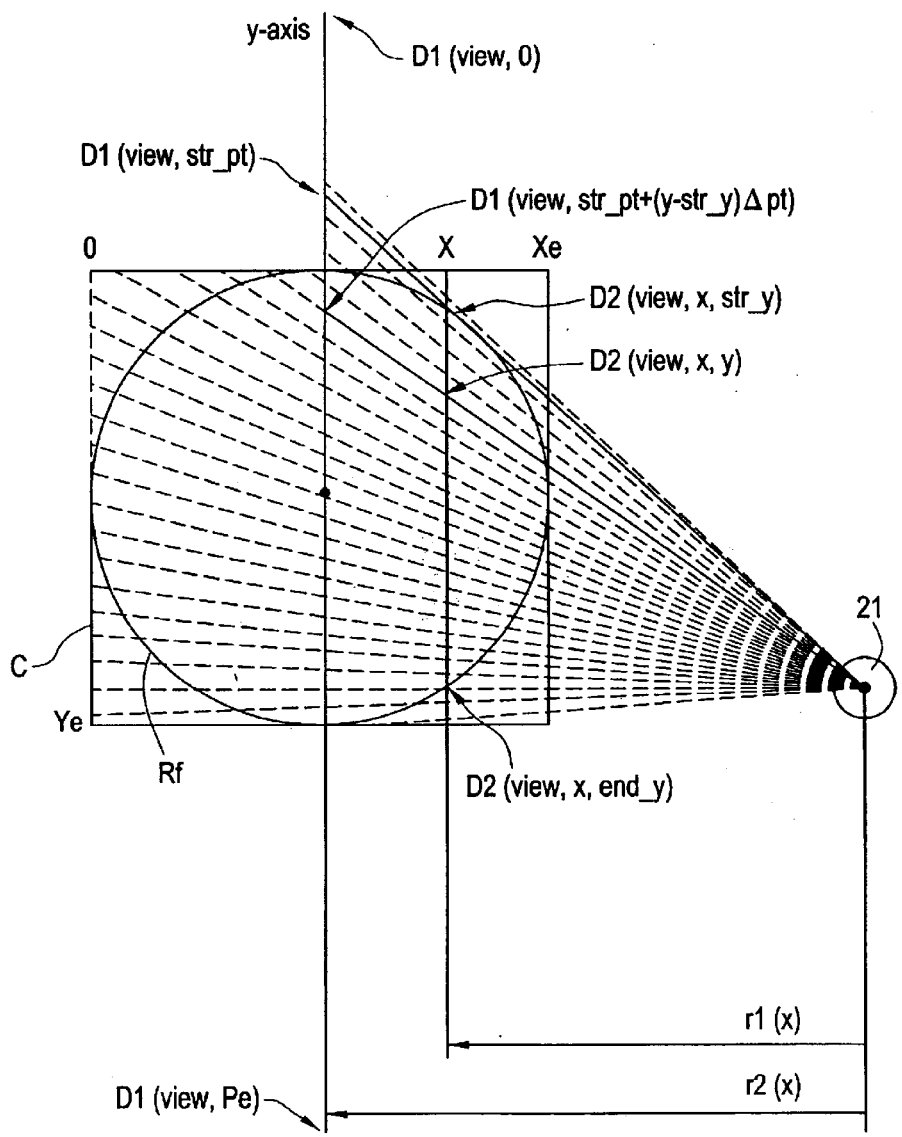
FIG. 12 is a diagram for explaining processing at Step S59.

Returning to FIG. 5, in Step S59, if the view angle falls within $45° \leq \text{view} < 135°$, a lookup table 32 corresponding to a view angle view=view−90° is referred to, and if the view angle falls within $225° \leq \text{view} < 315°$, a lookup table 32 corresponding to a view angle view=view−270° is referred to. At that time, interpretation of y into x, R(y) into R(x), str_x into st_y, and end_x into end_y is conducted, and pixel projection data D2(view, x, y) are calculated for x=0−x=Xe and for y=str_y−end_y, and added to the pixel projection data D2(x, y) stored in the storage device 7 according to the following equations:

$$D2(\text{view},x,y)=R(y) \times D1(\text{view},str\_pt+(y-str\_y) \times \Delta pt), \text{ and}$$

$$D2(x,y)=\Sigma D2(\text{view},x,y),$$

wherein Σ represents a summation over view. FIG. 12 is an explanatory diagram showing the processing at Step S59. Pixel projection data D2 is calculated along a straight line parallel to the y-axis from the axially projected data D1 on the projection axis x=Xe/2, and this process is repeated for x=0–Xe.

Figure 13:
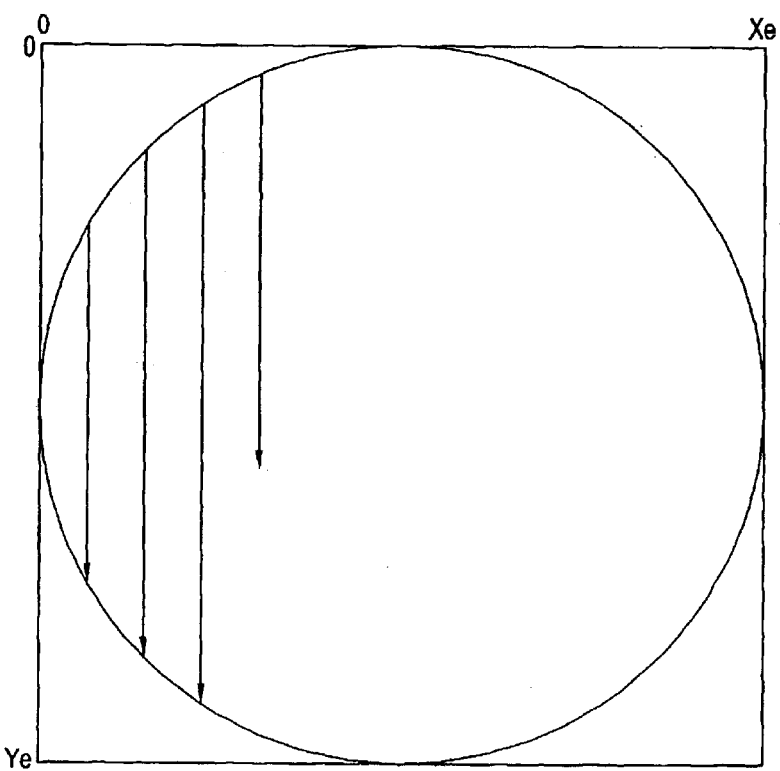
FIG. 13 is a diagram for explaining a pixel projection data storage section 70 in the storage device 7.

FIG. 13 is a conceptual diagram of the pixel projection data storage section 70 in the storage device 7. The pixel projection data D2 is added along a straight line parallel to the y-axis, and this process is repeated for x=0–Xe.

Returning to FIG. 5, in Step S62, data acquired in the pixel projection data storage section 70 are output as backprojection data D3(x, y). The backprojection processing is then terminated.

According to the backprojection processing as described above, the backprojection processing can be simplified and sped up. Moreover, only one pixel projection data storage section 70 is needed, although interpretation of parameters is needed in Step S59.

By the processing as described above, the backprojection processing can be simplified and sped up. Moreover, only one pixel projection data storage section 70 is needed, although interpretation of parameters is needed in Step S59.

Generally, X-ray tubes mounted on the gantry are expendables, and replacement is naturally required. At that time, an X-ray tube having the same specifications is used for the replacement, but alignment work for registering the position at which X-rays are generated by the X-ray tube (the focal spot position) is needed due to variation at the manufacturing stage.

However, if an amount of offset of the position is detected by some means, and the result of the detection is used to adjust the parameters for the pixel projection processing and axial projection processing (which is for determining the axially projected data D1) described above, the axially projected data D1 and pixel projection data D2 can be obtained to reconstruct an X-ray tomographic image with the amount of offset absorbed.

Hence, the following description will be made on a method relating to detection of the amount of offset in obtaining axially projected data D1 and pixel projection data D2, and a method of adjusting the pixel projection processing and axial projection processing. (These methods will be together referred to as an offset correction method hereinbelow).

<Offset Correction Method>

Figure 21:
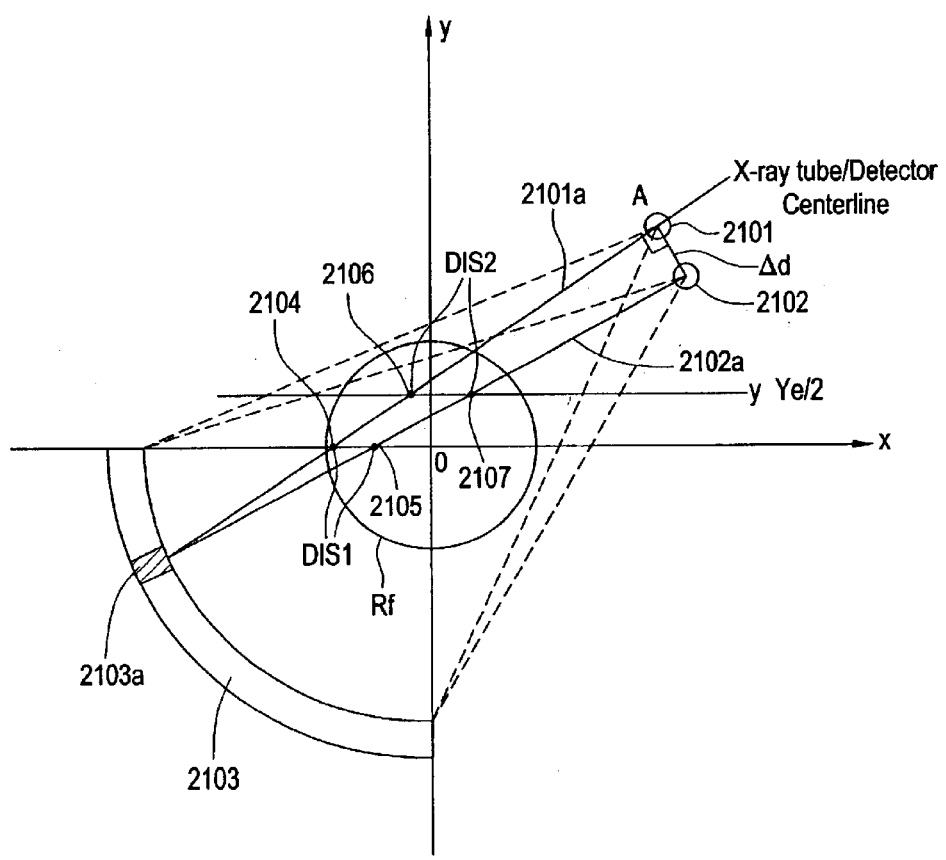
FIG. 21 is a diagram for explaining the principle of a method of determining proper backprojection data D3 and axially projected data D1 when using an X-ray tube (X-ray focal spot) having a positional relationship out of alignment with the detector.

FIG. 21 is a diagram for explaining the principle of a method of determining proper pixel projection data D2 and axially projected data D1 when using an X-ray tube (X-ray focal spot) having a positional relationship out of alignment with the detector. As used herein, proper pixel projection data D2 and axially projected data D1 refer to those that are determined based on projection data D0 obtained by an X-ray focal spot having a positional relationship in proper alignment with a detector, and the detector.

In FIG. 21, reference symbol Rf designates the aforementioned reconstruction region. Moreover, the center of the reconstruction region Rf is defined as an origin O, and x- and y-axes are defined as illustrated. In FIG. 21, reference numeral 2101 designates an X-ray focal spot A having a positional relationship in proper alignment with a detector 2103, and 2102 designates an X-ray focal spot having a positional relationship out of alignment with the detector 2103; and the position of the X-ray focal spot 2102 lies offset by Δd perpendicular to a centerline AO from the position of the X-ray focal spot 2101. Reference numeral 2101a designates an X-ray emitted from the X-ray focal spot 2101 toward a channel of interest 2103a in the detector 2103, and reference numeral 2102a designates an X-ray emitted from the X-ray focal spot 2102 toward the channel of interest 2103a in the detector 2103.

Since the X-ray 2101a emitted from the X-ray focal spot 2101 having a positional relationship in proper alignment with the detector 2103 toward the channel of interest 2103a intersects the x-axis at a point 2104, axially projected data D1 determined from projection data D0 obtained by the channel of interest 2103a represents a point 2104. (The method of determining the axially projected data D1 was described earlier.)

On the other hand, since the X-ray 2102a emitted from the X-ray focal spot 2102 having a positional relationship out of alignment with the detector 2103 toward the channel of interest 2103a intersects the x-axis at a point 2105, axially projected data D1 determined from projection data D0 obtained by the channel of interest 2103a represents a point 2105. (The method of determining the axially projected data D1 was described earlier.)

However, proper axially projected data D1 to be obtained by the channel of interest 2103a must represent the point 2104. Therefore, to determine the proper axially projected data D1 from the projection data D0 obtained by the X-ray focal spot 2102 and the detector 2103 in this case, offset correction processing is needed which replaces the axially projected data D1 at the point 2104 with the axially projected data D1 at the point 2105 (or in other words, which shifts the axially projected data D1 at the point 2104 in a (+)-direction of the x-axis by a distance DIS1 between the points 2104 and 2105 (i.e., an offset).

Thus, to determine the proper axially projected data D1 by the X-ray focal spot 2102 and the detector 2103, it is necessary to conduct processing which determines axially projected data D1 at the point 2104 using projection data obtained by a channel that detects an X-ray emitted from the X-ray focal spot 2102 and passing through the point 2104, and shifts the determined axially projected data D1 by the distance DIS1 in the (+)-direction of the x-axis. At that time, the distance DIS1 must also be determined beforehand.

Figure 23:
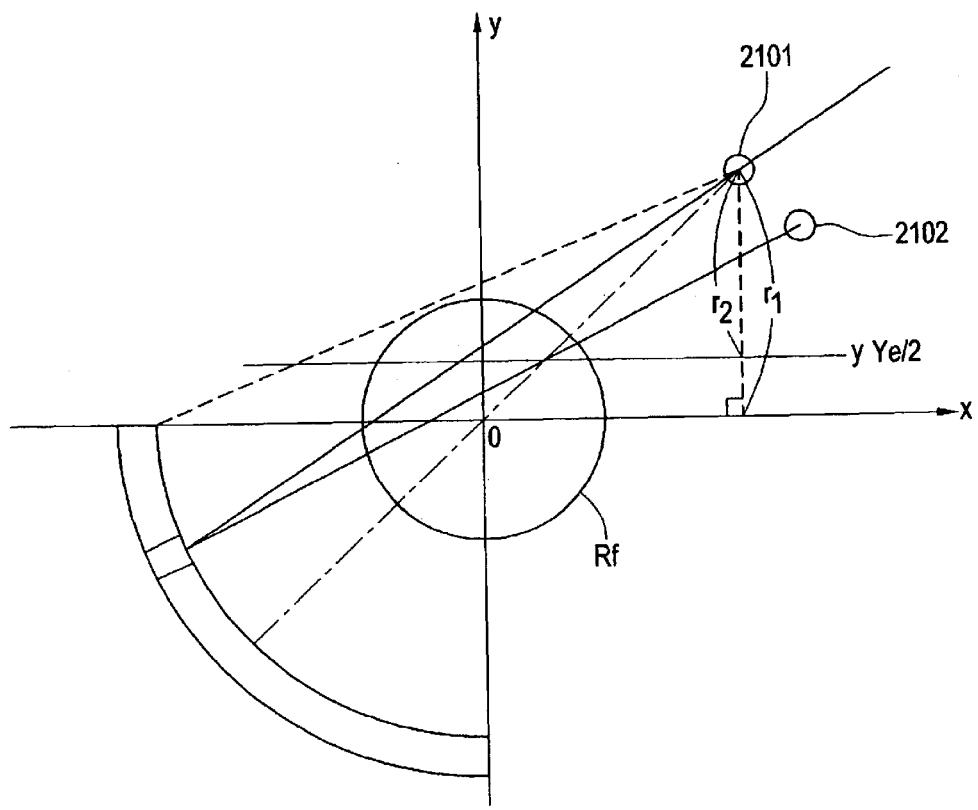
FIG. 23 is a diagram showing definitions of r1 and r2.

On the other hand, taking an example of y=Ye/2(y=r1−r2), and when determining proper pixel projection data D2 at y=r1−r2 by the X-ray focal spot 2102 and the detector 2103, offset correction processing which shifts pixel projection data D2 at a point 2106 in the (+)-direction of the x-axis by a distance DIS2 between points 2106 and 2107 (i.e., an offset) is similarly needed. At that time, the distance DIS2 must also be determined. Definitions of r1 and r2 are shown in FIG. 23.

Figure 22:
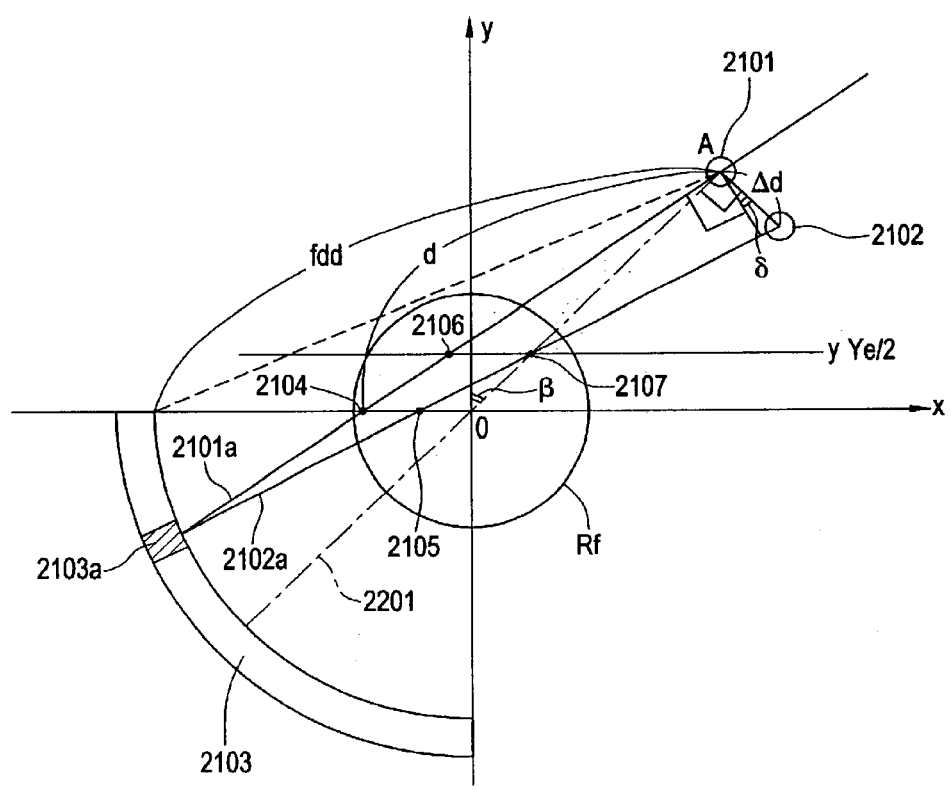
FIG. 22 is a diagram for explaining a method of calculating DIS1 and DIS2.

Now a method of determining the distances DIS1 and DIS2 (i.e., a method of determining offsets) will be described with reference to FIG. 22. FIG. 22 is a diagram for explaining the method of determining the distances DIS1 and DIS2, in which portions similar to those in FIG. 21 are designated by similar reference numerals. In FIG. 22, reference numeral 2201 designates an additional line linking the center point of the detector 2103 and the X-ray focal spot 2102. Reference symbol β designates an angle formed between the y-axis and the additional line 2201, and it can be obtained by a control system for the gantry rotating section from the zero-rotation position of an encoder signal of the gantry rotating motor. The position of the X-ray focal spot 2102 offsets from the position of the X-ray focal spot 2101 by a small distance Δd perpendicular to the centerline AO, and the angle formed by a line segment linking the X-ray focal spots 2101 and 2102 with the additional line 2201 is approximately 90°. This results from the fact that the offset of the position of the X-ray tube occurs in the direction of rotation of the X-ray focal spot and detector because the position of the X-ray focal spot offsets in parallel with a mount base for the X-ray tube.

Figure 24:
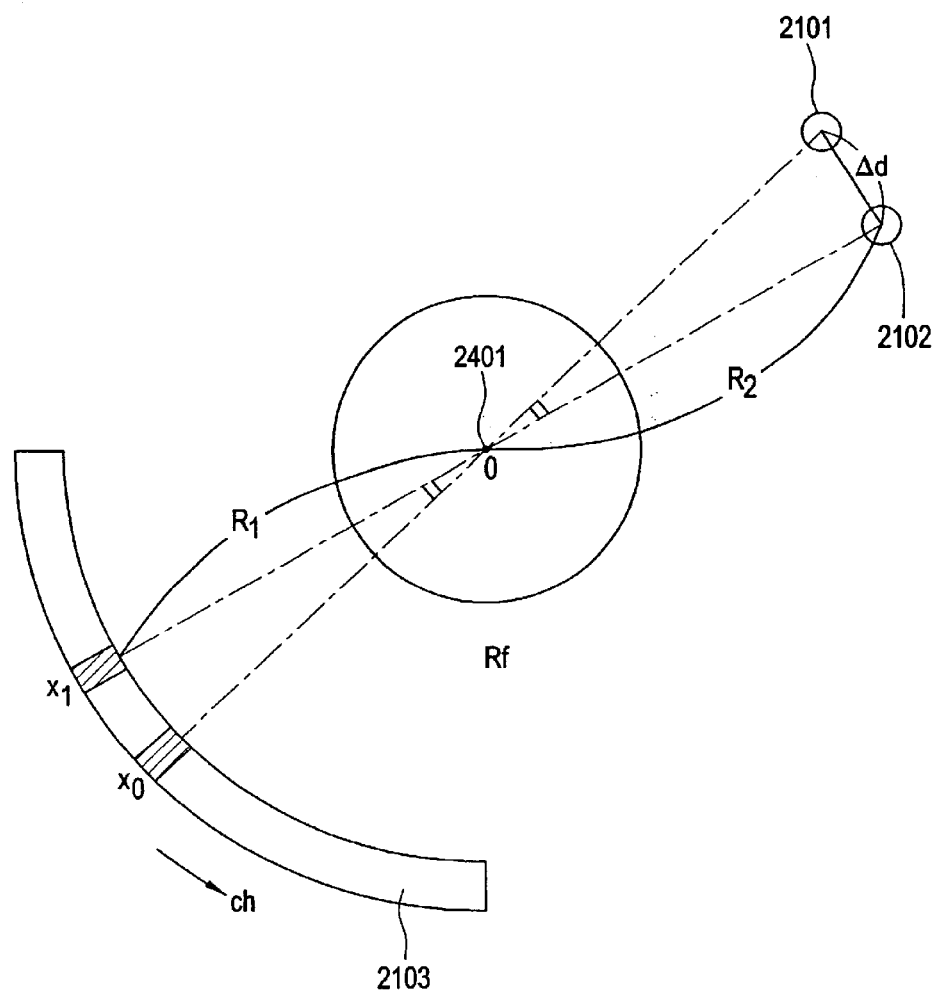
FIG. 24 is a diagram for explaining an exemplary method of obtaining Δd.

Although the method of determining (measuring) Δd is not particularly limited to any particular method, one example thereof is illustrated in FIG. 24 and will be described hereinbelow. Portions similar to those in FIG. 21 are designated by similar reference numerals. Reference numeral 2401 designates a gantry rotation center pin (a prespecified object to be imaged) which is positioned by a jig, and it is placed on an axis of rotation of the X-ray focal spot 2101 and detector 2103. Particularly, referring to FIG. 25, a phantom 2501 including the center pin 2401 is placed at one end of the imaging table 10 so that the position of the center pin 2410 lies at the axis of rotation of the X-ray focal spot 2101 and detector 2103.

Returning to FIG. 24, when X-rays are emitted at the X-ray focal spot 2101 in this condition, a channel (x0) lying at the center of the detector 2103 detects an X-ray passing through the center pin 2401. However, if X-rays are emitted at the X-ray focal spot 2102, a channel (x1) lying offset from the center of the detector 2103 detects the X-ray passing through the center pin 2401. Thus, Δd can be determined using the offset (Δx) and a ratio of R1 and R2. It should be noted that R1 and R2 are measured or designed beforehand.

Moreover, in FIG. 22, a distance from the X-ray focal spot 2101 to the detector 2103 is defined as fdd, and a distance from the X-ray focal spot 2101 to the x-axis along the X-ray 2101a is defined as d. Furthermore, an angle δ is defined as an angle formed between a line segment linking the X-ray focal spots 2101 and 2102 and a line segment forming an angle of 90° with the X-ray 2101a.

Based on such definitions, DIS1 can be calculated as follows:

$$DIS1 = ((fdd-d)/fdd) \times \Delta d \times \cos\delta \times 1/\cos(\beta+\delta). \quad (Eq.\ 1)$$

Thus, by calculating DIS1 using (Eq. 1), and shifting (correcting) by DIS1 the axially projected data D1 obtained by the method described earlier, proper axially projected data D1 can be obtained even when using an X-ray focal spot having a positional relationship out of alignment with the detector 2103.

Next, a method of calculating DIS2 will be described hereinbelow. In the condition shown in FIG. 22, two additional parameters r1 and r2 are defined. FIG. 23 shows the definitions of r1 and r2. In the condition shown in FIG. 22, a distance between the X-ray focal spot 2101 and the x-axis is r1, and a distance between the X-ray focal spot 2101 and y=Ye/2(y=r1−r2) is r2. It should be noted that although the following description will be made on a case of y=r1−r2, y may take any value between 0 and Ye. In this case, DIS2 can be calculated using DIS1 described above as follows:

$$DIS2 = \{fdd \times \cos(\beta+\delta) - r2\}/\{fdd \times \cos(\beta+\delta) - r1\} \times DIS1. \quad (Eq.\ 2)$$

Thus, by calculating DIS2 using (Eq. 2), and shifting (correcting) by DIS2 the pixel projection data D2 obtained by the method described earlier, proper pixel projection data D2 can be obtained even when using an X-ray focal spot having a positional relationship out of alignment with the detector 2103.

[Second Embodiment]

In the second embodiment, addition of pixel projection data D2 for a view angle range of $-45° \leq view < 45°$ and for a view angle range of $135° \leq view < 225°$ is conducted separately from addition of pixel projection data D2 for a view angle range of $45° \leq view < 135°$ and for a view angle range of $225° \leq view < 315°$, and backprojection data D3(x, y) are determined by finally adding the sums from the additions.

Figure 14:
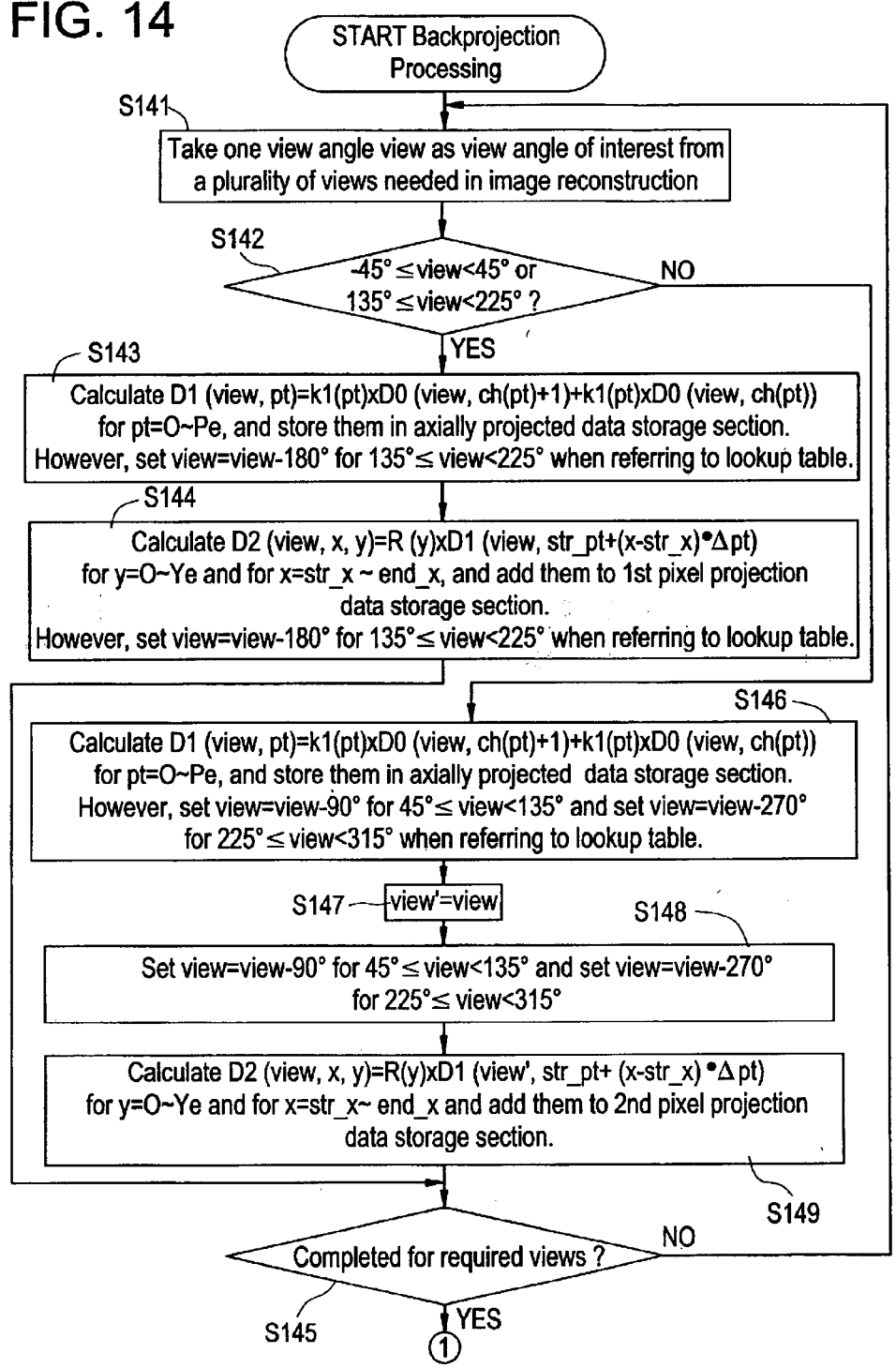
FIG. 14 is a flow chart showing backprojection processing in accordance with a second embodiment of the present invention.
Figure 15:
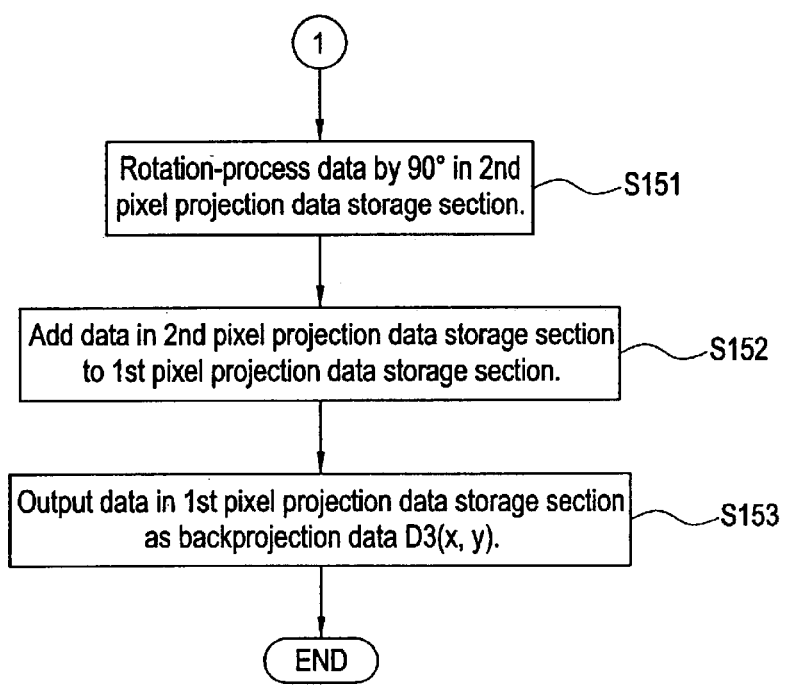
FIG. 15 is a flow chart showing the backprojection processing in accordance with the second embodiment of the present invention.

FIGS. 14 and 15 are flow charts showing backprojection processing in accordance with the second embodiment. In Step S141 in FIG. 14, one view angle view is taken as a view angle of interest from among a plurality of views needed in image reconstruction.

In Step S142, if the view angle of interest view is $-45° \leq view < 45°$ or $135° \leq view < 225°$, the process goes to S143; otherwise (i.e., if it is $45° \leq view < 135°$ or $225° \leq view < 315°$, goes to Step S146.

In Step S143, a lookup table 31 corresponding to a view angle view is referred to, to calculate axially projected data D1(view, pt) for pt=0−Pe according to the following equation:

$$D1(view, pt) = k1(pt) \times D0(view, ch(pt)+1) + k2(pt) \times D0(view, ch(pt)).$$

If ch(pt) is not defined for a certain pt, this pt is skipped and the next pt is taken. Moreover, for $135° \leq view < 225°$, a lookup table 31 corresponding to a view angle view=view−180° is referred to.

Figure 16:
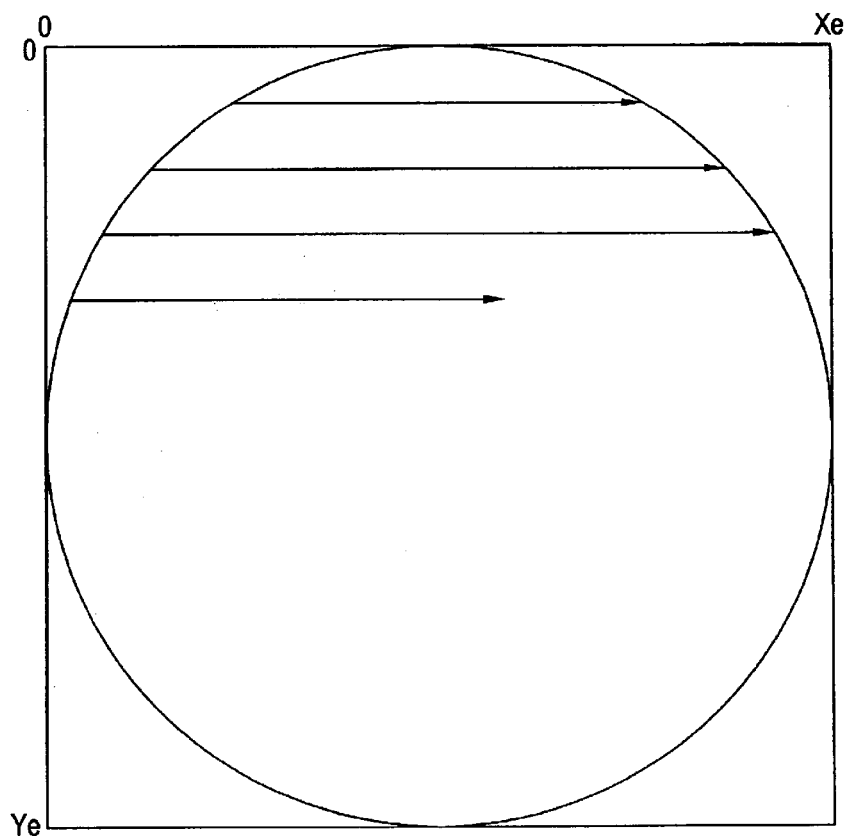
FIG. 16 is a conceptional diagram of a first pixel projection data storage section 71 in the storage device 7.

In Step S144, a lookup table 32 corresponding to the view angle view is referred to, and pixel projection data D2(view, x, y) are calculated for a range y=0−y=Ye, and for x=str_x−end_x, and added to pixel projection data D2(x, y) stored in a first pixel projection data storage section 71 shown in FIG. 16 in the storage device 7, according to the following equations:

$$D2(view, x, y) = R(y) \times D1(view, str\_pt + (x - str\_x) \times \Delta pt), \text{ and}$$

$$D2(x, y) = \Sigma D2(view, x, y),$$

wherein Σ represents a summation over view. For $135° \leq view < 225°$, a lookup table 32 corresponding to a view angle view=view−180° is referred to.

FIG. 16 is a conceptual diagram of the first pixel projection data storage section 71. The pixel projection data D2 is added along a straight line parallel to the x-axis, and this process is repeated for y=0−Ye.

In Step S145, if Steps S141–S149 have not been repeated for all views needed in image reconstruction, the process goes back to Step S141; and if Steps S141–S149 have been repeated for all views needed in image reconstruction, the process goes to Step S151 in FIG. 15.

In Step S146, if the view angle falls within $45° \leq view < 135°$, a lookup table 31 corresponding to a view angle view=view−90° is referred to, and if the view angle falls within $225° \leq view < 315°$, a lookup table 31 corresponding to a view angle view=view−270° is referred to. Then, axially projected data D1(view, pt) are calculated for pt=0−Pe similarly to Step S143 according to the following equation:

$$D1(view, pt) = k1(pt) \times D0(view, ch(pt)+1) + k2(pt) \times D0(view, ch(pt)).$$

If ch(pt) is not defined for a certain pt, this pt is skipped and the next pt is taken.

In Step S147, the current view is saved in view'. In Step S148, if the view angle falls within $45° \leq view < 135°$, the view angle is set to view=view−90°, and if the view angle falls within $225° \leq view < 315°$, the view angle is set to view=view−270°.

Figure 17:
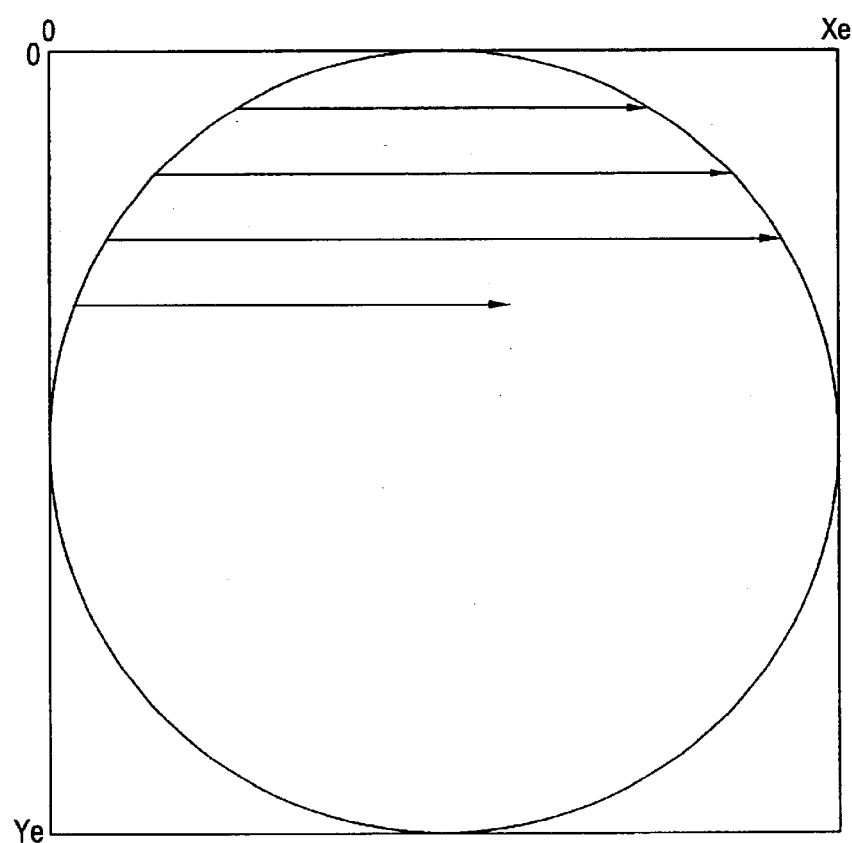
FIG. 17 is a conceptional diagram of a second pixel projection data storage section 72 in the storage device 7.

In Step S149, a lookup table 32 corresponding to the view angle view is referred to, and pixel projection data D2(view, x, y) are calculated for a range y=0−y=Ye, and for x=str_x−end_x, and added to pixel projection data D2(x, y) stored in a second pixel projection data storage section 72 shown in FIG. 17 in the storage device 7, according to the following equations:

$$D2(\text{view}',x,y)=R(y)\times D1(\text{view}',str\_pt+(x-str\_x)\times \Delta pt), \text{ and}$$

$$D2(x,y)=\Sigma D2(\text{view}',x,y),$$

wherein Σ represents a summation over view'. FIG. 17 is a conceptual diagram of the second pixel projection data storage section 72. The pixel projection data D2 is added along a straight line parallel to the x-axis, and this process is repeated for y=0–Ye.

Figure 18:
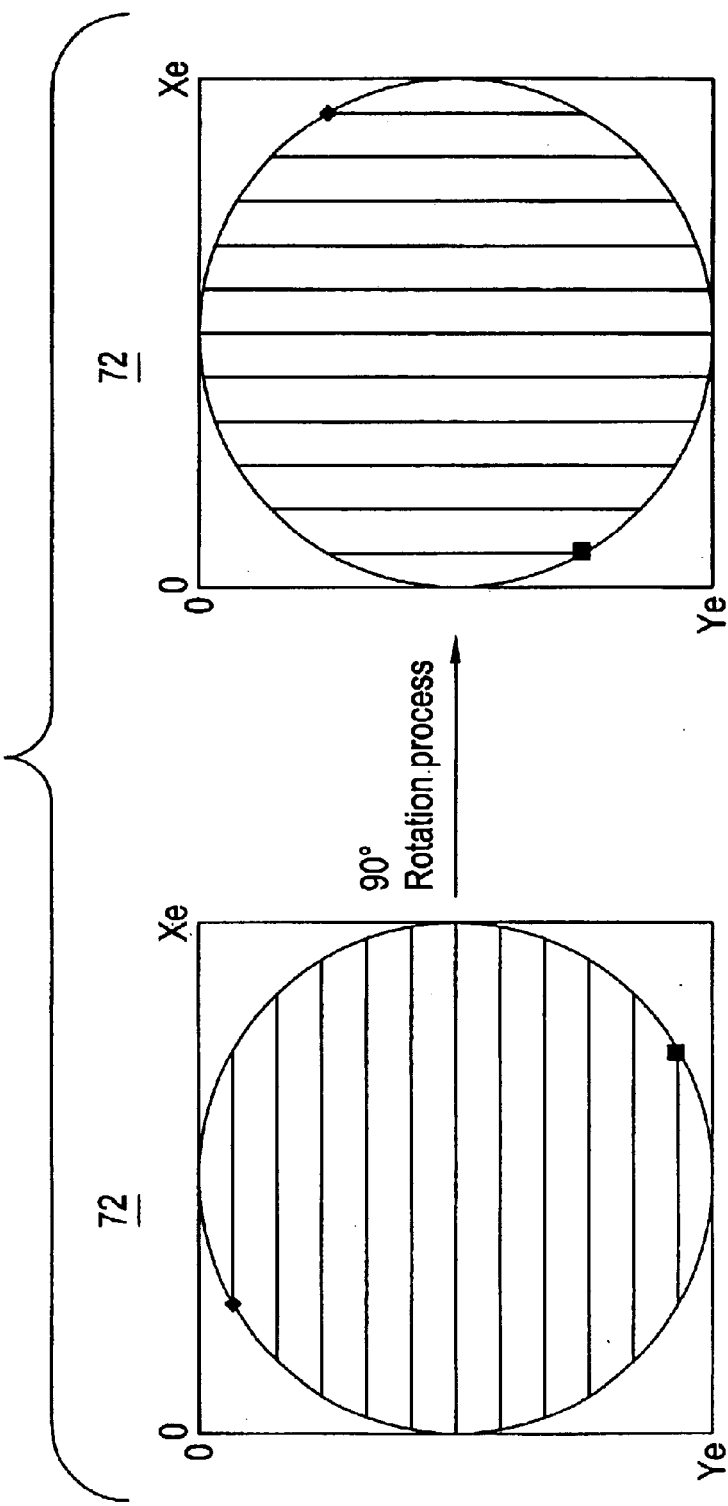
FIG. 18 is a diagram for explaining processing of rotating data in the second pixel projection data storage section 72 by 90°.
Figure 20:
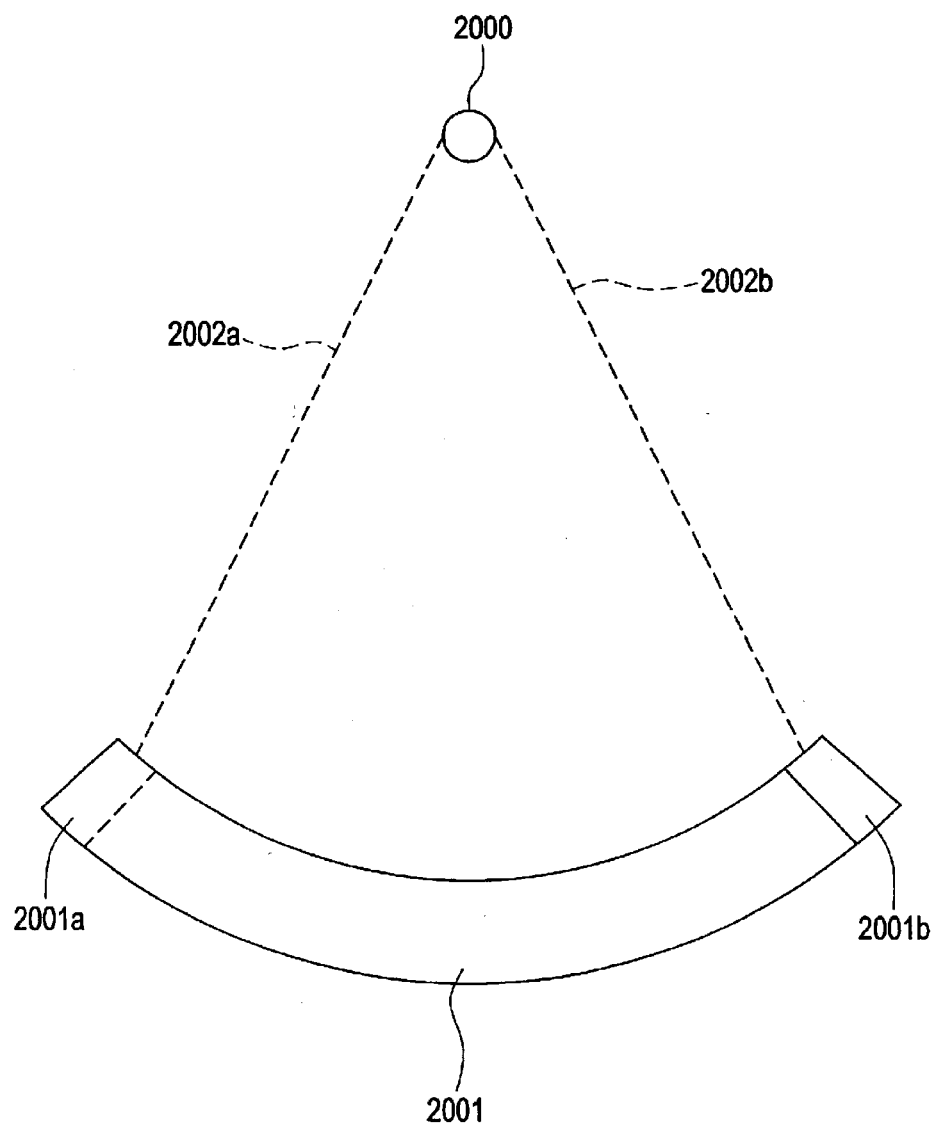
FIG. 20 is a diagram showing an X-ray focal spot and an X-ray detector having a positional relationship in proper alignment.

In Step S151 in FIG. 15, the data in the second pixel projection data storage section 72 is rotation-processed by 90°, as shown in FIG. 18. In Step S152, the data in the second pixel projection data storage section 72 are added to the data in the first pixel projection data storage section 71. In Step S153, data acquired in the first pixel projection data storage section 71 are output as backprojection data D3(x, y). The backprojection processing is then terminated.

According to the X-ray CT apparatus of the second embodiment, the backprojection processing can be simplified and sped up. Moreover, the need for interpretation of parameters at Step S149 is eliminated, although first and second separate pixel projection data storage sections 71 and 72 are used.

By performing the offset correction processing described in the first embodiment on the axially projected data D1 and pixel projection data D2 obtained using the method as described above, proper axially projected data D1 and backprojection data D3 can be obtained for final outputs.

[Third Embodiment]

While one axially projected datum D1 is calculated by interpolation calculation from two projection data D0 in the first and second embodiments, the one axially projected datum D1 is calculated by interpolation calculation from three projection data D0 in the third embodiment. In this case, a lookup table 31' as shown in FIG. 19 is employed, and the axially projected data D1 are calculated according to the following equation:

$$D1(\text{view},pt)=k1(pt)\times D0(\text{view},ch(pt)+2)$$

$$+k2(pt)\times D0(\text{view},ch(pt)+1).$$

$$+k3(pt)\times D0(\text{view},ch(pt))$$

According to the X-ray CT apparatus of the third embodiment, the backprojection processing can be simplified and sped up. Moreover, accuracy is improved.

By performing the offset correction processing described in the first embodiment on the axially projected data D1 obtained using the method as described above, proper axially projected data D1 can be obtained for a final output.

Many widely different embodiments of the invention may be configured without departing from the spirit and the scope of the present invention. It should be understood that the present invention is not limited to the specific embodiments described in the specification, except as defined in the appended claims.

What is claimed is:

1. An X-ray CT apparatus comprising:
   a gantry having an X-ray tube for emitting X-rays and a detector for detecting the X-rays emitted by said X-ray tube, said gantry outputting projection data D0 corresponding to an amount of the X-rays detected by said detector, represented by a view angle and a channel of said detector;
   an operating console having an axially projected data/pixel projection data calculating device for determining axially projected data D1 by projecting said projection data D0 obtained by said gantry onto a reference axis in a reconstruction region, and further determining pixel projection data D2 by projecting said axially projected data D1 onto coordinates of pixels constituting said reconstruction region, said operating console determining backprojection data D3 by adding said pixel projection data D2 determined by said axially projected data/pixel projection data calculating device for all views used in image reconstruction;
   an amount-of-offset measuring device for obtaining information indicative of an amount of offset of the position of said X-ray tube from a prespecified position; and
   a correcting device for correcting the axially projected data D1 or pixel projection data D2 determined by said axially projected data/pixel projection data calculating device using the information indicative of the amount of offset obtained by said amount-of-offset measuring device.

2. The X-ray CT apparatus of claim 1, wherein:
   said amount-of-offset measuring device comprises a phantom including a prespecified object to be imaged, and
   said information indicative of the amount of offset is obtained by: determining a positional offset of a channel from a center channel of said detector, said channel detecting an X-ray having passed through said phantom disposed on an axis of rotation of said X-ray tube and said detector, among the X-rays emitted by said X-ray tube toward said phantom and detected by said detector; and using said positional offset.

3. The X-ray CT apparatus of claim 1, wherein when said correcting device corrects the axially projected data D1,
   axially projected data D1 of a point at which an X-ray emitted from a position of said X-ray tube toward a channel of interest in said detector intersects said reference axis is replaced with axially projected data D1 of a point at which an X-ray emitted from said prespecified position toward said channel of interest intersects said reference axis after the corrective calculation.

4. The X-ray CT apparatus of claim 1, wherein said correcting device determines a distance between a first point at which an X-ray emitted from a position of said X-ray tube toward a channel of interest in said detector intersects said reference axis and a second point at which an X-ray emitted from said prespecified position toward said channel of interest intersects said reference axis, and replaces axially projected data D1 of said first point with axially projected data D1 of said second point after the corrective calculation.

5. The X-ray CT apparatus of claim 1, wherein when said correcting device corrects the pixel projection data D2,
   pixel projection data D2 of a point at which an X-ray emitted from a position of said X-ray tube toward a channel of interest in said detector intersects an axis of interest in said reconstruction region is replaced with pixel projection data D2 of a point at which an X-ray emitted from said prespecified position toward the channel of interest in said detector intersects said axis of interest after the corrective calculation.

6. The X-ray CT apparatus of claim 1, wherein said correcting device determines a distance between a first point at which an X-ray emitted from a position of said X-ray tube toward a channel of interest in said detector intersects said axis of interest and a second point at which an X-ray emitted from said prespecified position toward said channel of interest intersects said axis of interest, and replaces pixel projection data D2 of said first point with pixel projection data D2 of said second point after the corrective calculation.

7. A method of controlling an X-ray CT apparatus, said X-ray CT apparatus being comprised of:

a gantry having an X-ray tube for emitting X-rays and a detector for detecting the X-rays emitted by said X-ray tube, said gantry outputting projection data D0 corresponding to an amount of the X-rays detected by said detector, represented by a view angle and a channel of said detector; and an operating console having an axially projected data/pixel projection data calculating device for determining axially projected data D1 by projecting said projection data D0 obtained by said gantry onto a reference axis in a reconstruction region, and further determining pixel projection data D2 by projecting said axially projected data D1 onto coordinates of pixels constituting said reconstruction region, said operating console determining backprojection data D3 by adding said pixel projection data D2 determined by said axially projected data/pixel projection data calculating device for all views used in image reconstruction, said method comprising:

an amount-of-offset measuring step of obtaining information indicative of an amount of offset of the position of said X-ray tube from a prespecified position; and a correcting step of correcting the axially projected data D1 or pixel projection data D2 determined at said axially projected data/pixel projection data calculating step using the information indicative of the amount of offset obtained at said amount-of-offset measuring step.

8. The method of controlling an X-ray CT apparatus of claim 7, wherein said amount-of-offset measuring step comprises:

using a phantom including a prespecified object to be imaged, and determining a positional offset of a channel from a center channel of said detector, said channel detecting an X-ray having passed through said phantom disposed on an axis of rotation of said X-ray tube and said detector, among the X-rays emitted by said X-ray tube toward said phantom and detected by said detector, and using said determined positional offset to obtain said information indicative of the amount of offset.

9. The method of controlling an X-ray CT apparatus of claim 7, wherein when the axially projected data D1 is corrected at said correcting step, axially projected data D1 of a point at which an X-ray emitted from a position of said X-ray tube toward a channel of interest in said detector intersects said reference axis is replaced with axially projected data D1 of a point at which an X-ray emitted from said prespecified position toward said channel of interest intersects said reference axis after the corrective calculation.

10. The method of controlling an X-ray CT apparatus of claim 7, wherein said correcting step comprises determining a distance between a first point at which an X-ray emitted from a position of said X-ray tube toward a channel of interest in said detector intersects said reference axis and a second point at which an X-ray emitted from said prespecified position toward said channel of interest intersects said reference axis, and replacing axially projected data D1 of said first point with axially projected data D1 of said second point after the corrective calculation.

11. The method of controlling an X-ray CT apparatus of claim 7, wherein when the pixel projection data D2 is corrected at said correcting step, pixel projection data D2 of a point at which an X-ray emitted from a position of said X-ray tube toward a channel of interest in said detector intersects an axis of interest in said reconstruction region is replaced with pixel projection data D2 of a point at which an X-ray emitted from said prespecified position toward the channel of interest in said detector intersects said axis of interest after the corrective calculation.

12. The method of controlling an X-ray CT apparatus of claim 7, wherein said correcting step comprises determining a distance between a first point at which an X-ray emitted from a position of said X-ray tube toward a channel of interest in said detector intersects said axis of interest and a second point at which an X-ray emitted from said prespecified position toward said channel of interest intersects said axis of interest, and replacing pixel projection data D2 of said first point with pixel projection data D2 of said second point after the corrective calculation.

13. A program executing a method of controlling an X-ray CT apparatus, said X-ray CT apparatus being comprised of:

a gantry having an X-ray tube for emitting X-rays and a detector for detecting the X-rays emitted by said X-ray tube, said gantry outputting projection data D0 corresponding to an amount of the X-rays detected by said detector, represented by a view angle and a channel of said detector; and an operating console having an axially projected data/pixel projection data calculating device for determining axially projected data D1 by projecting said projection data D0 obtained by said gantry onto a reference axis in a reconstruction region, and further determining pixel projection data D2 by projecting said axially projected data D1 onto coordinates of pixels constituting said reconstruction region, said operating console determining backprojection data D3 by adding said pixel projection data D2 determined by said axially projected data/pixel projection data calculating device for all views used in image reconstruction, said program comprising:

a program for an amount-of-offset measuring step of obtaining information indicative of an amount of offset of the position of said X-ray tube from a prespecified position; and a program for a correcting step of correcting the axially projected data D1 or pixel projection data D2 determined at said axially projected data/pixel projection data calculating step using the information indicative of the amount of offset obtained at said amount-of-offset measuring step.

14. The program executing a method of controlling an X-ray CT apparatus of claim 13, wherein said amount-of-offset measuring step comprises:

using a phantom including a prespecified object to be imaged, and determining a positional offset of a channel from a center channel of said detector, said channel detecting an X-ray having passed through said phantom disposed on an axis of rotation of said X-ray tube and said detector, among the X-rays emitted by said X-ray tube toward said phantom and detected by said detector, and using said determined positional offset to obtain said information indicative of the amount of offset.

15. The program executing a method of controlling an X-ray CT apparatus of claim 13, wherein when the axially projected data D1 is corrected at said correcting step, axially projected data D1 of a point at which an X-ray emitted from a position of said X-ray tube toward a channel of interest in said detector intersects said reference axis is replaced with axially projected data D1 of a point at which an X-ray emitted from said prespecified position toward said channel of interest intersects said reference axis after the corrective calculation.

16. The program executing a method of controlling an X-ray CT apparatus of claim 13, wherein said correcting step comprises determining a distance between a first point at which an X-ray emitted from a position of said X-ray tube toward a channel of interest in said detector intersects said reference axis and a second point at which an X-ray emitted from said prespecified position toward said channel of interest intersects said reference axis, and replacing axially projected data D1 of said first point with axially projected data D1 of said second point after the corrective calculation.

17. The program executing a method of controlling an X-ray CT apparatus of claim 13, wherein when the pixel projection data D2 is corrected at said correcting step, pixel projection data D2 of a point at which an X-ray emitted from a position of said X-ray tube toward a channel of interest in said detector intersects an axis of interest in said reconstruction region is replaced with pixel projection data D2 of a point at which an X-ray emitted from said prespecified position toward the channel of interest in said detector intersects said axis of interest after the corrective calculation.

18. The program executing a method of controlling an X-ray CT apparatus of claim 13, wherein said correcting step comprises determining a distance between a first point at which an X-ray emitted from a position of said X-ray tube toward a channel of interest in said detector intersects said axis of interest and a second point at which an X-ray emitted from said prespecified position toward said channel of interest intersects said axis of interest, and replacing pixel projection data D2 of said first point with pixel projection data D2 of said second point after the corrective calculation.

* * * * *